US008445544B2

(12) United States Patent
Turecek et al.

(10) Patent No.: US 8,445,544 B2
(45) Date of Patent: May 21, 2013

(54) HYDROLYSABLE POLYMERIC FMOC-LINKER

(75) Inventors: Peter Turecek, Klosterneuburg (AT); Juergen Siekmann, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 643 days.

(21) Appl. No.: 12/688,461

(22) Filed: Jan. 15, 2010

(65) Prior Publication Data

US 2010/0121034 A1    May 13, 2010

Related U.S. Application Data

(62) Division of application No. 12/215,218, filed on Jun. 25, 2008.

(60) Provisional application No. 60/937,169, filed on Jun. 26, 2007, provisional application No. 61/123,263, filed on Apr. 7, 2008.

(51) Int. Cl.
  *A61K 31/015*    (2006.01)
(52) U.S. Cl.
  USPC ........................ 514/764; 514/13.7; 514/14.2
(58) Field of Classification Search
  None
  See application file for complete search history.

(56) References Cited

U.S. PATENT DOCUMENTS 6,680,295 B1 *    1/2004    Arimura .................. 514/8.3

FOREIGN PATENT DOCUMENTS

| WO | WO-2004/089280 | 10/2004 |
| WO | WO-2005/014655 | 2/2005 |
| WO | WO-2006/071801 | 7/2006 |
| WO | WO-2008-074032 | 6/2008 |

OTHER PUBLICATIONS

Tsubery H. et al; "PRolonging the action of protein and peptide drugs by a novel approach of reversible polyethylene glycol modification." J. Bio. Chem. (2004) 279(37) p. 38118-38124.*
Spector, R.; "Fatty acid transport through the blood-brain barrier." J. Neurochem. (1998) 50(2) p. 639-643.*
NCBI protein database accession No. AF205361_1 for human growth hormone.*
Hirabayashi, Y et al; "Studies of thio acids II. The reaction of steric esters with sodium hydrosulfide." J. Bull. Soc. Japan. (1965) 38(2) p. 320-322.*
Stryer, L. "Biochemistry." ISBN 0-7167-1843-X, 1988.*
International Search Report for PCT/EP2008/005155 dated Nov. 12, 2008.
Written Opinion for PCT/EP2008/005155.
Gregoriadis et al., Improving the therapeutic efficacy of peptides and proteins: A role for polysialic acids. *Int. J. Pharma.* 300 (1-2): 125-30 (2005).
Jain et al., Polysialylation: The natural way to improve the stability and pharmacokinetics of protein and peptide drugs. <http://www/lipoxen.co.uk/media/48760/dds%20and%20s%20pp3-9.pdf> Retrieved May 22, 2007.
Saenko et al., Strategies towards a longer acting factor VIII. *Haemophilia*, 12(3): 42-51 (2006).
Shechter et al., Albumin-insulin conjugate releasing insulin slowly under physiological conditions: A new concept for long-acting insulin. *Bioconj. Chem.* 16(4): 913-20 (2005).
Shechter et al., New technologies to prolong life-time of peptide and protein drugs in vivo. *Int. J. Peptide Res. Therap.* 13(1-2): 105-17 (2007).
Tsubery et al., Prolonging the action of protein and peptide drugs by a novel approach of reversible polyethylene glycol modification. *J. Biol. Chem.* 279: 38118-24 (2004).

* cited by examiner

*Primary Examiner* — Cecilia J Tsang
*Assistant Examiner* — Fred Reynolds
(74) *Attorney, Agent, or Firm* — Marshall, Gerstein & Borun LLP

(57)    ABSTRACT

The invention relates to Fmoc (9-fluorenyl-methoxycarbonyl)-based polymeric conjugates. These conjugates are useful for extending the in-vivo circulation of protein and peptide drugs.

10 Claims, 5 Drawing Sheets

HYDROLYSABLE POLYMERIC FMOC-LINKER

CROSS REFERENCE TO RELATED APPLICATIONS

This application is a divisional application of U.S. patent application Ser. No. 12/215,218, filed Jun. 25, 2008, which in turn claims the benefit of U.S. Provisional Application No. 60/937,169, filed Jun. 26, 2007 and U.S. Provisional Application No. 61/123,263, filed Apr. 7, 2008, the disclosures of each is incorporated by reference in its entirety.

FIELD OF THE INVENTION

The present invention relates to the preparation of a hydrolysable linker, which is bound to at least one semi-synthetic polymer. These hydrolysable linker are useful for extending the in-vivo circulation of protein and peptide drugs.

BACKGROUND OF THE INVENTION

Most protein or peptide drugs are short-lived and have often a short circulatory half-life in vivo. Considering that protein or peptide drugs are not absorbed orally, prolonged maintenance of therapeutically active drugs in the circulation is a desirable feature of obvious clinical importance.

An attractive strategy for improving clinical properties of protein or peptide drugs is a modification of the drugs with polymers e.g. polyalkylene-oxides (Roberts et al., Advan Drug Rev. 54, 459-476 (2002)) or polysaccharides like polysialic acid (Fernandes et al., Biochim Biophys Acta 1341, 26-34 (1997)), dextranes or hydroxyl alkyl starch. (All documents cited in the specification are incorporated by reference.)

The modification with poly(ethylene glycol) (PEG) has been known for a while. However, modification of proteins with PEG often leads to reduction of the activity of the protein.

Polysialic acid (PSA), also known as colominic acid (CA), is a natural occurring polysaccharide. It is a homopolymer of N-acetylneuraminic acid with α(2→8) ketosidic linkage and contains vicinal diol groups at its non-reducing end. PSA is negatively charged and is a natural constituent of the human body. It can easily be produced from bacteria in large quantities with pre-determined physical characteristics (U.S. Pat. No. 5,846,951). Being chemically and immunologically identical to polysialic acid in the human body, bacterial polysialic acid is non-immunogenic even when coupled to proteins. Unlike other polymers (e.g.; PEG), polysialic acid is biodegradable.

However, to date no therapeutic compound comprising a polypeptide conjugated to an acidic monosaccharide such as PSA is commercially available.

Short PSA polymeric chains with only 1-4 sialic acid units have also been synthesized (Kang et al., Chem. Commun., 227-228 (2000); Ress et al., Current Organic Synthesis 1, 31-46 (2004)).

Several hydrolysable or degradable linkers comprising PEG moieties have been suggested.

U.S. Pat. No. 6,515,100, describes PEG and related polymer derivatives, having weak, hydrolytically unstable linkages U.S. Pat. No. 7,122,189 describes releasable PEG-linkers based on bis-N-2-hydroxyethyl glycine groups (bicine).

WO 04/089280 and WO 06/138572 describe hydrolysable fluorene-based PEG constructs.

After conjugation of these linkers to protein drugs, the protein-polymer conjugate can be regarded as a prodrug and the activity of the protein can be released from the conjugate via a controlled release mechanism. Using this concept improved pharmacokinetic properties of the drug can be obtained (Zhao et al., Bioconjugate Chem. 17, 341-351 (2006)).

SUMMARY OF THE INVENTION

The present invention provides a hydrolysable linker, which is bound to at least one semi-synthetic biopolymer, wherein the hydrolysable linker is conjugated to a protein or peptide drug in order to improve its in-vivo properties such as the in-vivo circulation.

The present invention provides a compound of the general formula 1:

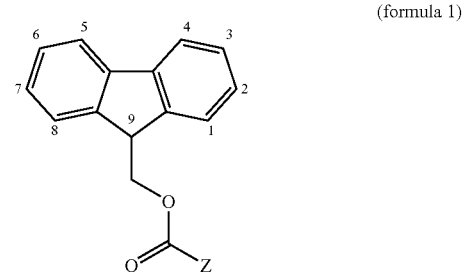

(formula 1)

wherein Z a leaving group and at least one of position 1, 2, 3, 4, 5, 6, 7 or 8 is bound to radical Y.

Y is a radical containing a semi-synthetic biopolymer, which is bound to a N-succinimidyl moiety.

In addition to being bound to radical Y the compound of formula 1 may optionally be bound to radical X in at least one of the available position 1, 2, 3, 4, 5, 6, 7 or 8.

X is —$SO_3$—$R^3$.

$R^3$ is selected from the group consisting of hydrogen, ($C_1$-$C_8$)-alkyl and ($C_1$-$C_8$)-alkyl-$R^4$.

$R^4$ is a polymer.

DETAILED DESCRIPTION OF THE INVENTION

Figure 1:
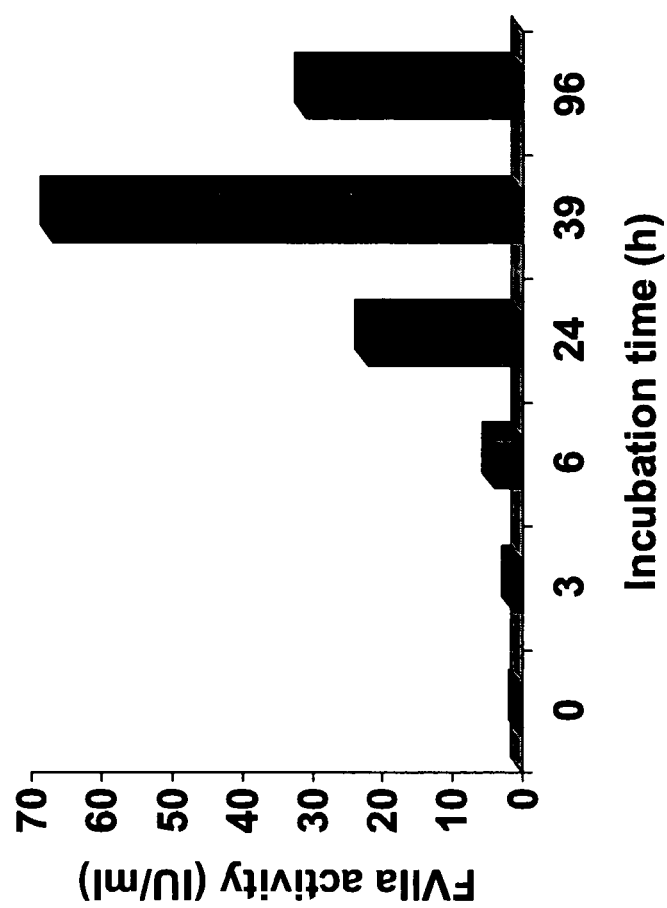
FIG. 1 shows the in-vitro hydrolysis of a FVIIa-PSA conjugate at pH 8.3. The release of the FVIIa activity was measured with the Staclot-assay (Diagnostica Stago, Asnières, France).

The present invention provides a hydrolysable linker, which is bound to at least one semi-synthetic biopolymer, wherein the hydrolysable linker can be further conjugated to a protein or peptide drug in order to improve their in-vivo properties such as in-vivo circulation. The activity of the protein or peptide drug can be released from the conjugate via a controlled release mechanism.

The following paragraphs provide general definitions and definition of various chemical moieties that make up the compounds according to the invention and are intended to apply uniformly through-out the specification and claims unless an otherwise expressly set out definition provides a broader definition.

"$C_1$-$C_8$-alkyl" refers to monovalent alkyl groups having 1 to 8 carbon atoms. This term is exemplified by groups such as methyl, ethyl, propyl, butyl, hexyl and the like. Linear and branched alkyls are included.

"Leaving groups" refers to groups, which are capable of reacting with a nucleophile present on the protein or peptide drug that forms the conjugate. This term is exemplified by groups such as N-hydroxysuccimimidyl, N-hydroxybenzotriazolyl, halogen, N-hydroxyphthalimidyl, p-nitrophenoxy, imidazolyl, thiazolidinyl thione, O-acyl ureas or other suitable leaving groups will be apparent to those of ordinary skill. For the purpose of the present invention, the protein or peptide drug thus contains one or more groups for displacement, such as an amine. Protein or peptide drug are plasma proteins or blood coagulation factors such as FVIII, VWF, FVIIa and FIX.

A "semi-synthetic biopolymer" refers to a manufactured organic polymer, which is based on a naturally occurring polymer. A semi-synthetic biopolymer may also be functionalized by reactive groups in order to conjugate these functionalized semi-synthetic biopolymers to other compounds. This term "semi-synthetic biopolymer" is exemplified by linear or branched polymers such as carbohydrates, specifically such as polysaccharides. Examples of polysaccharides are PSA (polysialic acid) and HAS (hydroxyalkylstarch).

"Hydrolysable" linker refers to a linker system, in which the protein is released in native form. The protein is released and the linker is split off completely. Synonyms for hydrolysable are "degradable" or "releasable" linkers.

The present invention provides a compound of the general formula 1:

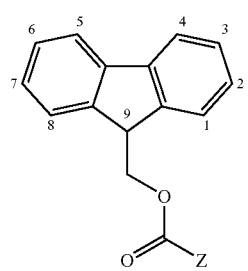

(formula 1)

wherein Z a leaving group and at least one of position 1, 2, 3, 4, 5, 6, 7 or 8 is bound to radical Y.

Y is a radical containing a semi-synthetic biopolymer, which is bound to a N-succinimidyl moiety.

In addition to being bound to radical Y the compound of formula 1 may optionally be bound to radical X in at least one of the available position 1, 2, 3, 4, 5, 6, 7 or 8.

X is —$SO_3$—$R^3$.

$R^3$ is selected from the group consisting of hydrogen, ($C_1$-$C_8$)-alkyl and ($C_1$-$C_8$)-alkyl-$R^4$.

$R^4$ is a polymer. Examples are hydrophilic polymers such as poly(ethylene glycol) (PEG).

In one embodiment, the invention relates to a compound of formula 1, wherein Z is an N-succinimidyl ester and at least one of position 1, 2, 3, 4, 5, 6, 7 or 8 is bound to radical Y, wherein Y is:

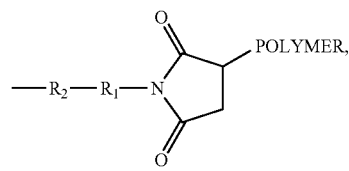

wherein POLYMER is a semi-synthetic biopolymer, preferably with a molecular weight of 1,000 Da to 300,000 Da.

In one embodiment the molecular weight is 5,000-25,000, preferably 5,000-10,000.

In another embodiment said semi-synthetic biopolymer is a carbohydrate, preferably a polysaccharide, preferably comprising at least 3 units of a monosaccharide.

In one embodiment said polysaccharide comprises between 2-200 units, preferably between 10-100 units of a monosaccharide.

In one embodiment the semi-synthetic biopolymer is a PSA derivative.

In another embodiment the semi-synthetic biopolymer is bound to the succinimidyl moiety via a thioether linkage.

$R^1$ is at each occurrence independently a ($C_1$-$C_8$)-alkyl.

In one embodiment $R^1$ is at each occurrence independently selected from the group consisting of methyl, ethyl, propyl, butyl, and hexyl.

$R^2$ is independently selected from the group consisting of —C(O)NR—, —C(O)NR—($C_1$-$C_8$)-alkyl-NR—, —NRC(O)— and —NRC(O)—($C_1$-$C_8$)-alkyl-NR, wherein R is independently either hydrogen or ($C_1$-$C_8$)-alkyl.

In one embodiment $R^2$ is —C(O)NH—.

In another embodiment $R^2$ is —NHC(O)—.

In one embodiment the compound of formula 1 is bound to radical Y in at least one of position 1, 2, 3 or 4.

In another embodiment the compound of formula 1, is bound to radical Y in at least one of position 1, 2, 3, or 4 and is further bound to radical X in at least one of position 5, 6, 7, or 8.

In another embodiment the compound of formula 1, is bound to at least one radical Y in at least one of position 2 or 3 is further bound to radical X in at least one of position 7 or 8.

In another embodiment the compound of formula 1 is bound to radical Y in positions 2 and 7.

In another embodiment the compound of formula 1 is bound to radical Y and radical X in positions 2 and 7, respectively.

In another embodiment the compound of formula 1 is:
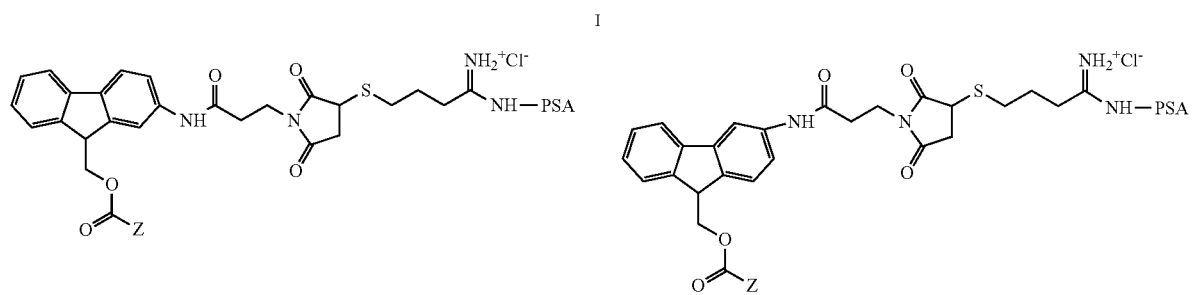
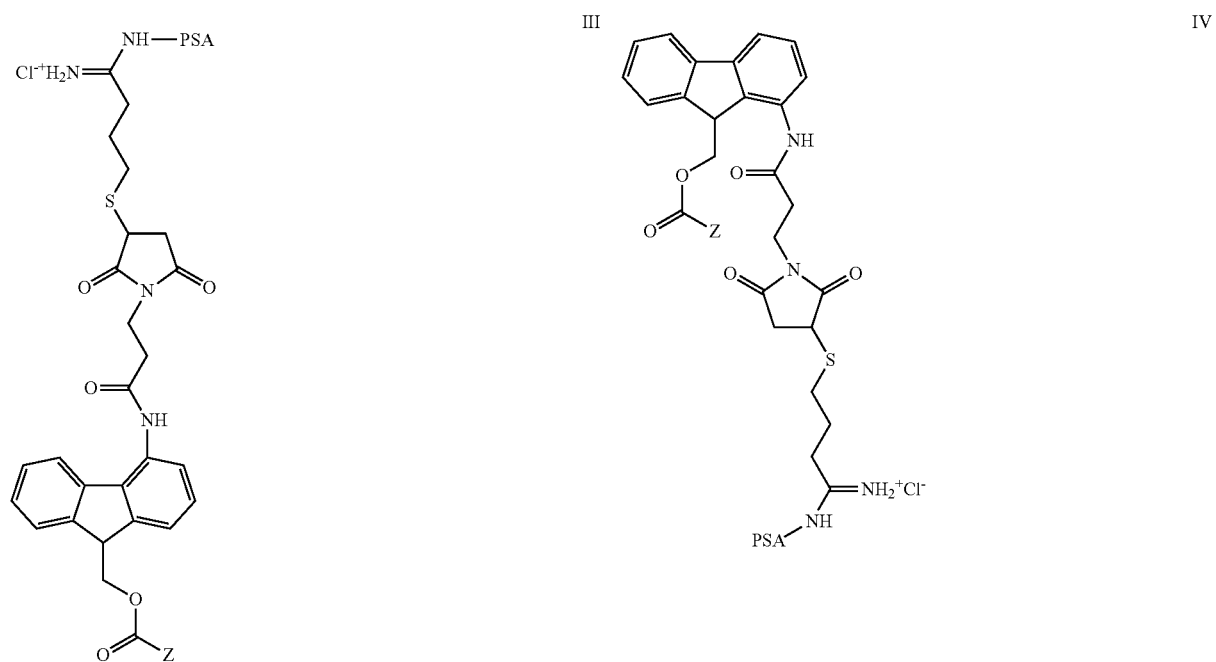
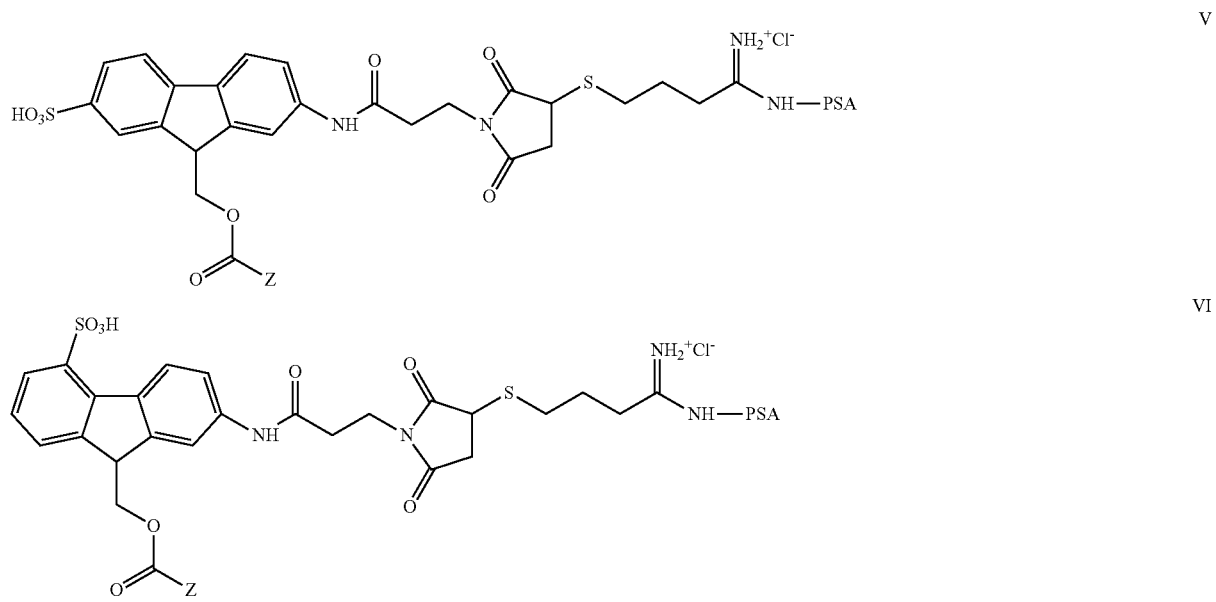

-continued
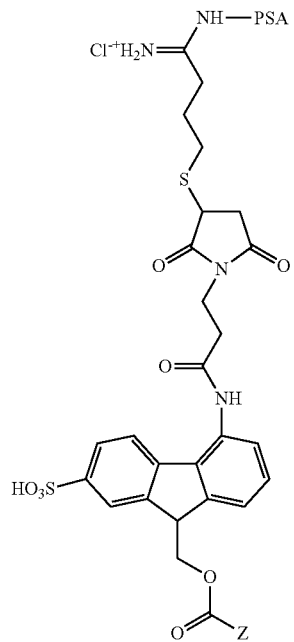
VII
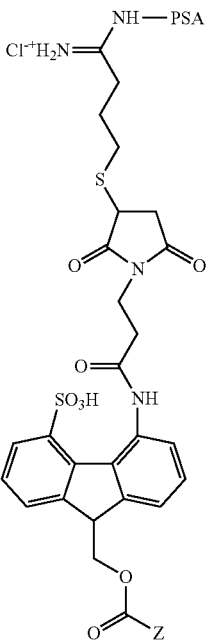
VIII
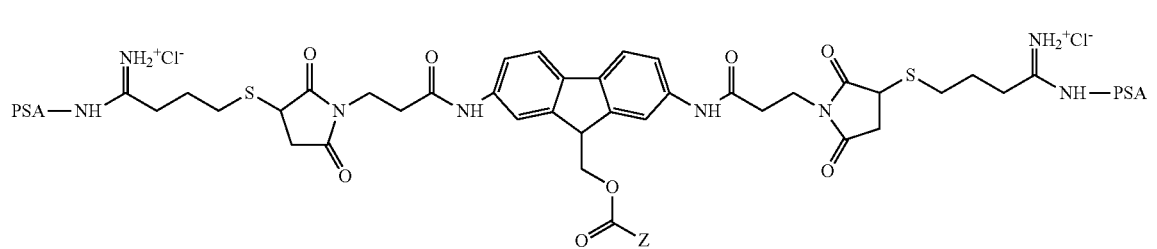
IX
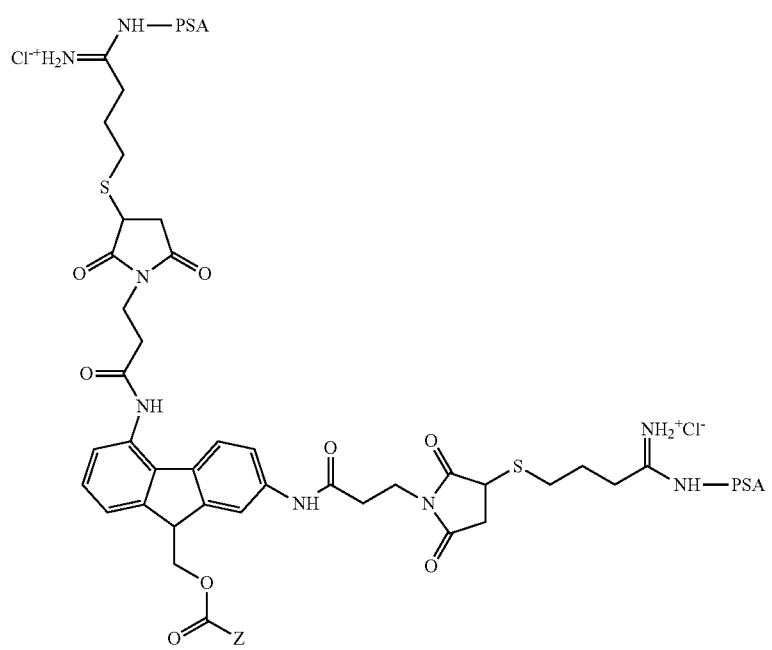
X

XI

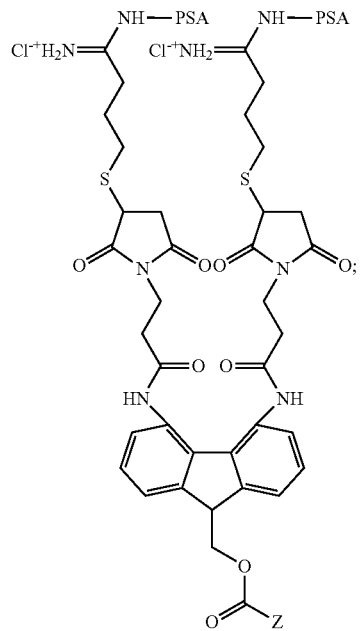

In a further embodiment, the invention relates to the preparation of a compound of formula 1.

Tsubery et al., J Biol. Chem. 279, 38118-38124 (2004) described the synthesis of a hydrolysable PEG-linker for derivatization of proteins based on the Fmoc (9-fluorenyl-methoxycarbonyl)-moiety. The synthesis of MAL-FMS-OSU (9-Hydroxymethyl-2-(amino-3-maleimido-propionate)-7-sulfo fluorene N-hydroxysuccinimidyl carbonate) is described. The synthetic scheme below illustrates the synthetic steps for the preparation of a compound of formula 1 as an example, starting from a MAL-FMS-OSU derivative.

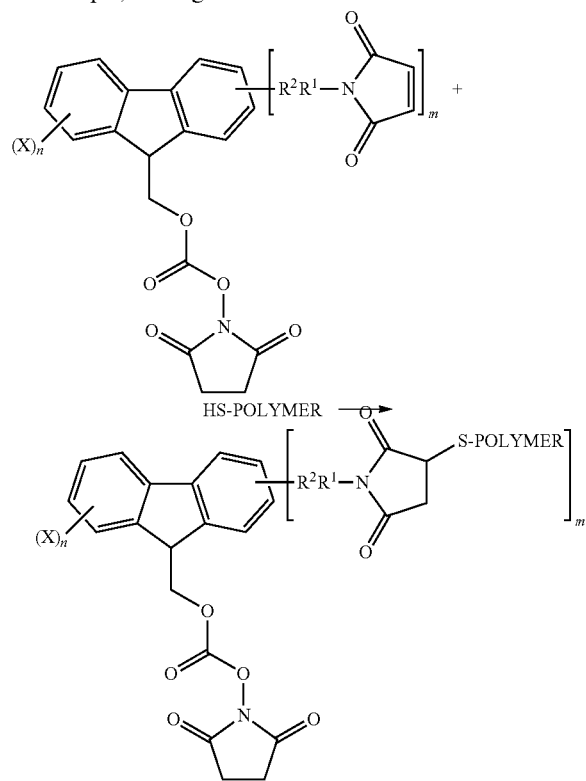

wherein

POLYMER is a semi-synthetic biopolymer;

$R^1$ is at each occurrence independently a ($C_1$-$C_8$)-alkyl;

$R^2$ is independently selected from the group consisting of —C(O)NR—, —C(O)NR—($C_1$-$C_8$)-alkyl-NR—, —NRC(O)— and —NRC(O)—($C_1$-$C_8$)-alkyl-NR, wherein R is independently either hydrogen or $C_1$-$C_8$-alkyl.

R is independently either hydrogen or ($C_1$-$C_8$)-alkyl;

X is —$SO_3$—$R^3$;

$R^3$ is independently selected from the group consisting of hydrogen, ($C_1$-$C_8$)-alkyl and ($C_1$-$C_8$)-alkyl-$R^4$;

$R^4$ is a polymer;

n is an integer selected from 0, 1, 2, 3, or 4; and m is an integer selected from 1, 2, 3, or 4.

HS-POLYMER is a thiol-derivatized semi-synthetic biopolymer, such as

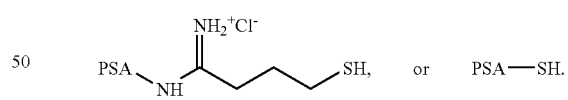

A compound of formula 2 can be easily reacted with a protein or peptide drug containing one or more groups for displacement, such as amines. Preferred protein or peptide drug are blood coagulation factors such as FVIII, VWF, FVIIa, FIX.

Figure 2:
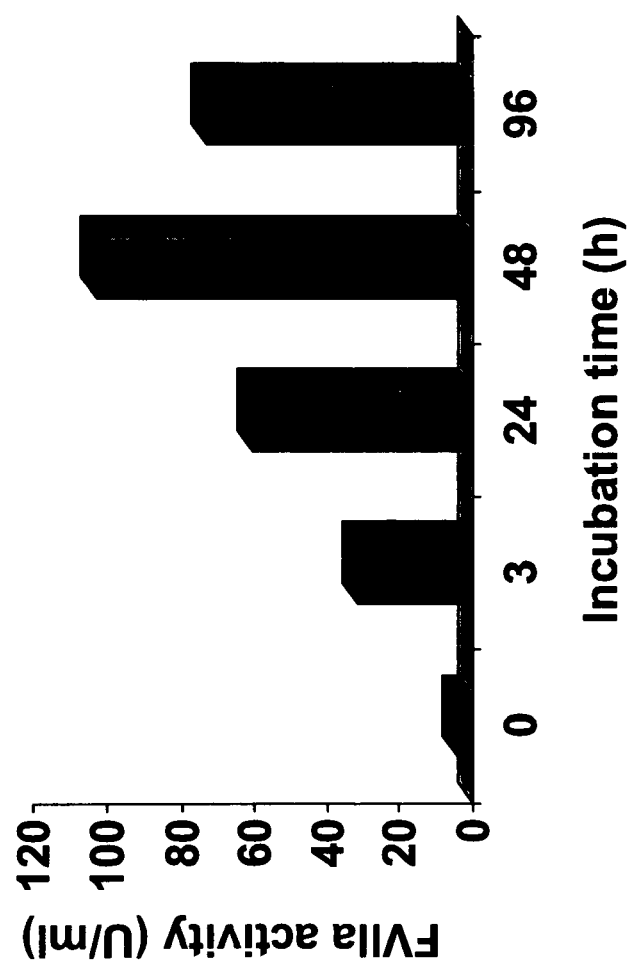
FIG. 2 shows the shows the in-vitro hydrolysis of a FVIIa-trimer PSA conjugate at pH 8.3. The release of the FVIIa activity was measured with the Staclot-assay (Diagnostica Stago, Asnières, France).
Figure 3:
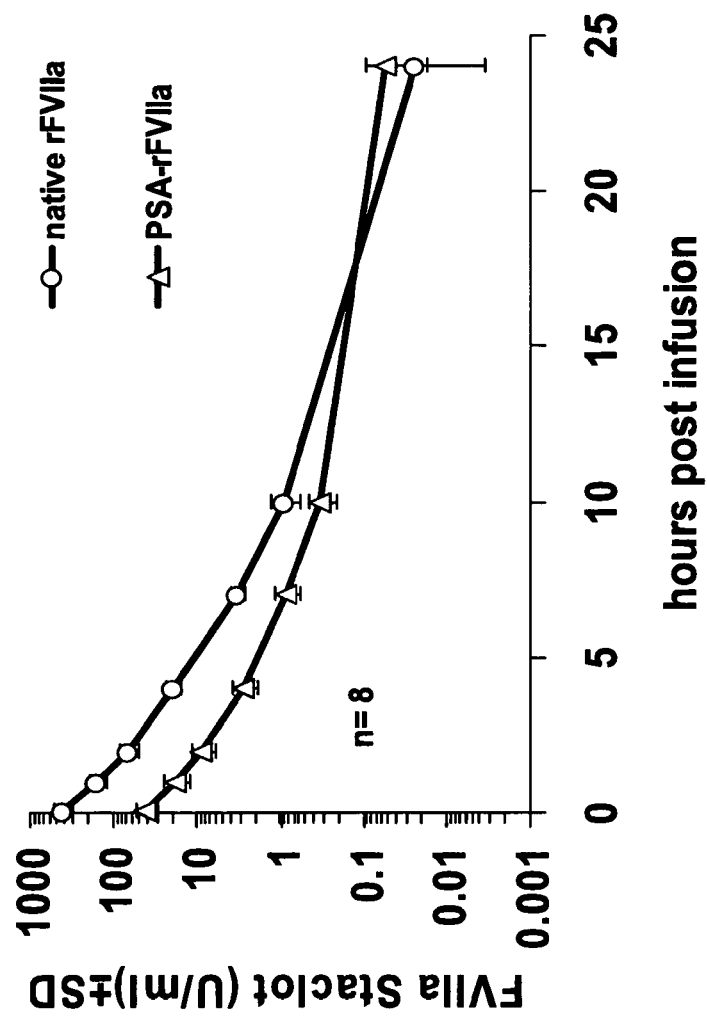
FIG. 3 shows FVIIa activity in plasma measured with a clotting assay (Staclot, Diagnostica Stago, Asnières, France). For FVIIa clotting activity the dose adjusted area under curve (AUC) was 0.014 for unmodified rFVIIa and increased to 0.015 for rFVIIa-conjugate (0-infinity). The terminal half-life increased from 2.3 to 4.4 hours and the mean residence time (MRT) from 1.4 to 2.4 hours.
Figure 4:
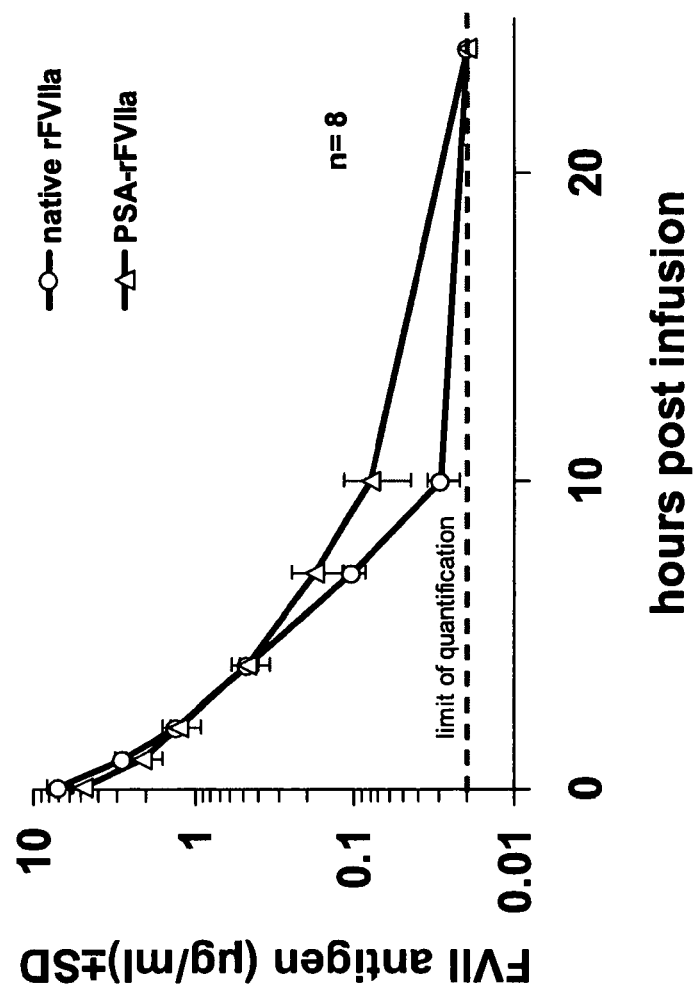
FIG. 4 shows the determination of the FVIIa antigen by ELISA with a polyclonal anti-human FVII antibody. For the antigen the dose adjusted AUC (0-infinity) increased from 0.010 (unmodified rFVIIa) to 0.014 (rFVIIa-conjugate), the terminal half life increased from 1.4 to 2.3 hours and the MRT from 1.5 to 2.2 hours.

Protein and peptide drugs modified according to the above protocol have a significantly increased in-vivo circulation. The hydrolysability of the linker allows that the activity can be regained after hydrolysis, by release of the protein in its native form. An example is shown in FIGS. 1 and 2. The restoration of the biological activity of a protein conjugate is shown in FIGS. 3 and 4.

The present invention is illustrated by the following examples without being limited thereto.

EXAMPLES

Example 1

Preparation of PSA Containing Terminal SH Groups

Polysialic acid (Sigma) was oxidized with $NaIO_4$ (Fernandes et al., Biochim Biophys Acta 1341, 26-34 (1997)), and a terminal aldehyde group was formed. Then a reductive amination step with $NH_4Cl$ was carried out as described in WO 05/016973 and the Schiff Base was reduced with $NaCNBH_3$ to form $PSA-NH_2$ containing a terminal amino group. Subsequently a reaction with 2-iminothiolane (Pierce 26101) was performed according to the instruction leaflet of the manufacturer to prepare a modified PSA containing a terminal SH group. The molarity of the generated SH-groups was determined using Ellmans reagent. In addition the same procedure was used to introduce a SH-group in a N-Acetylneuramic acid trimer, which was obtained from TimTec, LLC, Newark, USA.

Example 2

Conjugation of rFVIIa with PSA Using the MAL-FMS-OSU Linker

To 15 ml of a solution of rFVIIa (0.7 mg/ml) in 50 mM phosphate buffer pH 7.2 the bifunctional linker MAL-FMS-OSU (prepared as outlined by Tsubery et al., J Biol. Chem. 279, 38118-38124 (2004)) was added (concentration: 0.5 mg/mg protein) and incubated at R.T. for 30 min. Then derivatized PSA containing a terminal SH group was prepared according to Example 1. The PSA derivative was added to the mixture (concentration: 10 mg PSA-SH/mg protein) and incubated for additional 2 hours. Then the reaction was stopped by adding an aqueous solution of 0.1 M glycine (final concentration 10 mM) and 5 mM cysteine (end concentration 0.5 mM). The free reagents were separated from the rFVIIa-PSA conjugate by ion exchange chromatography using a QHyperD F 50 µm resin (BioSepra) and a Pharmacia XK-10 column (Pharmacia XK 10; h=10 cm). The PSA-rFVIIa containing solution was applied to the column, which was subsequently washed with 10 CV equilibration buffer (20 mM sodium citrate, 20 mM NaCl, pH 6.5). Then the polysialylated rFVIIa was eluted with elution buffer (20 mM sodium citrate, 500 mM NaCl, pH 6.1). The eluate contained 0.06 mg/ml protein, the evidence of bound PSA in the conjugate was proven by the resorcinol assay (Svennerholm; Biochim Biophys Acta 24: 604-11 (1957)). For release of the activity of rFVIIa in the conjugate 450 µl of the eluate was added to 50 µl 1 M TRIS-buffer pH 8.3 and the release of the FVIIa activity was measured (Staclot, Diagnostica Stago, Asnières, France). The results are illustrated in FIG. 2.

Example 3

Conjugation of rFVLLa with Trimer PSA Using the MAL-FMS-OSU Linker

To 15 ml of a solution of rFVIIa (0.7 mg/ml) in 50 mM phosphate buffer pH 7.2 the bifunctional linker MAL-FMS-OSU (prepared as outlined by Tsubery et al., J Biol. Chem. 279, 38118-38124 (2004)) was added (concentration: 0.07 mg/mg protein) and incubated at R.T. for 30 min. Then trimer PSA (TimTec, LLC, Newark, USA) was derivatized as described in Example 1 to introduce a free SH-group. The trimer PSA-SH derivative was added to the mixture (concentration: 0.43 mg trimer PSA-SH/mg protein) and incubated for additional 2 hours. Then the reaction was stopped by adding an aqueous solution of 0.1 M glycine (final concentration 10 mM) and 5 mM cysteine (end concentration 0.5 mM). The free reagents were separated from the rFVIIa-PSA conjugate by ion exchange chromatography using a QHyperD F 50 µm resin (BioSepra) and a Pharmacia XK-10 column (Pharmacia XK 10; h=10 cm). The PSA-rFVIIa containing solution was applied to the column, which was subsequently washed with 10 CV equilibration buffer (20 mM sodium citrate, 20 mM NaCl, pH 6.5). Then the polysialylated rFVIIa was eluted with elution buffer (20 mM sodium citrate, 500 mM NaCl, pH 6.1). The eluate contained 0.06 mg/ml protein, the evidence of bound PSA in the conjugate was proven by the resorcinol assay (Svennerholm et al., Biochim Biophys Acta 24, 604-11 (1957)). For release of the activity of rFVIIa in the conjugate 450 µl of the eluate was added to 50 µl 1 M TRIS-buffer pH 8.3 and the release of the FVIIa activity was measured (Staclot, Diagnostica Stago, Asnières, France). The results are illustrated in FIG. 1.

Example 4

Conjugation of Human Serum Albumin with PSA Using the MAL-FMS-OSU Linker

Human Serum Albumin (HSA) is incubated with the bifunctional linker Mal-FMS-OSU linker (prepared as outlined by Tsubery et al., J Biol. Chem. 279, 38118-38124 (2004)) in 25 mM sodium acetate buffer, pH 6.2 for 1 hour. Then the excess linker is separated by gelfiltration using Sephadex G-25 (GE-Healthcare) using the same buffer system The protein containing fractions are collected and PSA-SH (prepared according to Example 1) is added. The mixture is incubated for 2 hours at R.T. Then the conjugate is purified by anion-exchange chromatography using DEAE-Sepharose FF (GE Healthcare). The Protein-PSA conjugate is eluted with 25 mM sodium acetate buffer pH 4.5. The conjugate containing fractions are pooled and concentrated by ultrafiltration using a 10K membrane. Then the solution is diafiltrated against 25 mM sodium acetate buffer, pH 6.2.

Example 5

Pharmacokinetic of rFVIIa-PSA-Conjugate in Normal Rats

A rFVIIa-PSA conjugate was prepared according to Example 2 using a concentration of MAL-FMS-OSU of 0.05 mg/mg protein. 8 normal rats (4 male, 4 female) were anaesthetized and the rFVIIa-PSA-conjugate in buffer (1.3 g/L glycylglycine, 3 g/L sodium chloride, 30 g/L mannitol, 1.5 g/L $CaCl_2 \times 2H_2O$, 0.1 g/L Tween 80, pH 5.5) was applied by intravenous injection into the tail vein in a volume dose of 10 ml per kg (1200 μg protein/kg). Unmodified rFVIIa in a dose of 1200 μg protein/kg was used as control in 8 normal rats (4 male, 4 female). Blood samples were taken from the tail artery 5 minutes, 1 hour, 2, 4, 7, 10 and 24 hours after substance application and citrated plasma was prepared and frozen for further analysis.

FVIIa activity in plasma was measured with a clotting assay (Staclot, Diagnostica Stago, Asnières, France), FVII antigen was determined with an ELISA (polyclonal anti-human FVII antibody). The results were evaluated statistically. For FVIIa clotting activity the dose adjusted area under curve (AUC) was 0.014 for unmodified rFVIIa and increased to 0.015 for rFVIIa-conjugate (0-infinity). The terminal half-life increased from 2.3 to 4.4 hours and the mean residence time (MRT) from 1.4 to 2.4 hours. For the antigen the dose adjusted AUC (0-infinity) increased from 0.010 (unmodified rFVIIa) to 0.014 (rFVIIa-conjugate), the terminal half life increased from 1.4 to 2.3 hours and the MRT from 1.5 to 2.2 hours. All calculations were carried out by use of a statistical program (program R: A language and environment for statistical computing. R Foundation for Statistical Computing, Vienna, Austria, ISBN 3-900051-07-0, URL http://www.R-project.org). The pharmacokinetic results are illustrated in FIGS. 3 and 4.

Example 6

Pharmacokinetic of rFVIIa-Trimer-PSA-Conjugate in Normal Rats rFVIIa-trimer-PSA conjugate was prepared according to Example 3 using a MAL-FMS-OSU concentration of 0.05 mg/mg protein. 6 normal rats (3 male, 3 female) were anaesthetized and the rFVIIa-trimer-PSA-conjugate in buffer (1.3 g/L glycylglycine, 3 g/L sodium chloride, 30 g/L mannitol, 1.5 g/L $CaCl_2 \times 2H_2O$, 0.1 g/L Tween 80, pH 5.5) was applied by intravenous injection into the tail vein in a volume dose of 10 ml per kg (1200 µg protein/kg). Unmodified rFVIIa in a dose of 1200 µg protein/kg was used as a control in 6 normal rats (3 male, 3 female). Blood samples were taken from the tail artery 5 minutes, 1 hour, 2, 4, 7, 10 and 24 hours after substance application and citrated plasma was prepared and frozen for further analysis.

Figure 5:
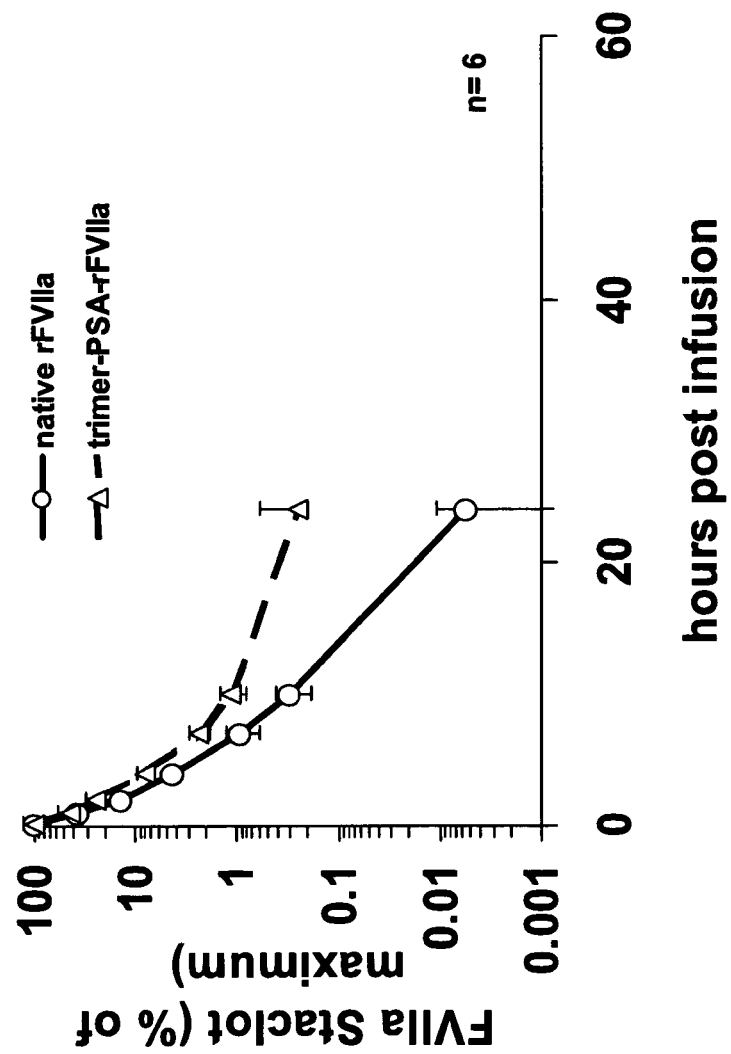
FIG. 5 shows FVIIa activity in plasma, measured with a clotting assay (Staclot, Diagnostica Stago, Asnières, France). The pharmacokinetic of rFVIIa-trimer-PSA conjugates is improved (-○-) compared to native rFVIIa (--Δ--).

FVIIa activity in plasma was measured with a clotting assay (Staclot, Diagnostica Stago, Asnières, France) and the elimination curve was constructed. The improved pharmacokinetic of the rFVIIa-trimer-PSA conjugate is illustrated in FIG. 5.

Example 7

Conjugation of rFIX with PSA Using the MAL-FMS-OSU Linker

To 0.6 ml of a solution of recombinant FIX (8 mg/ml) in 20 mM Hepes buffer, pH 7.4 the bifunctional linker MAL-FMS-OSU (prepared as outlined by Tsubery et al., J Biol. Chem. 279, 38118-38124 (2004)) was added (concentration: 0.07 mg/mg protein) and incubated at R.T. for 30 min. Derivatized PSA containing a terminal SH group was prepared according to Example 1. The PSA derivative was added to the mixture (concentration: 32 mg PSA-SH/mg protein—100 fold molar excess) and incubated for additional 2 hours at R.T. The reaction was stopped by adding an aqueous solution of 0.1 M glycine (final concentration 10 mM) and 5 mM cysteine (end concentration 0.5 mM). The free reagents were separated from the rFIX-PSA conjugate by Hydrophobic Interaction Chromatography using a prepacked Butyl Sepharose column (HiTrap Butyl FF 5 ml, GE Healthcare). A buffer containing 5 M NaCl (50 mM Hepes-buffer, 5M NaCl, 0.01% Tween 80, 6.7 mM $CaCl_2$, pH 6.9) was added to the PSA-rFIX containing solution to give a final concentration of 3M NaCl. This mixture was applied to the column, which was subsequently washed with 10 CV equilibration buffer (50 mM Hepes-buffer, 3M NaCl, 0.01% Tween 80, 6.7 mM $CaCl_2$, pH 6.9) and the elution of the rFIX-PSA conjugate was carried out with 50 mM Hepes-buffer, pH 7.4, containing 6.7 mM $CaCl_2$. After elution of the conjugate the pH was adjusted to pH 6.9. The eluate contained 0.24 mg/ml protein as measured by the BCA-assay, the evidence of bound PSA in the conjugate was proven by the resorcinol assay (Svennerholm, Biochim Biophys Acta 24, 604-611 (1957)). In a final step the eluate was concentrated 10 fold by ultrafiltration/diafiltration (UF/DF) using a 30 kD membrane (regenerated cellulose/Millipore) against 20 mM Hepes, 50 mM NaCl, 1 mM $CaCl_2$, pH 7.4.

Example 8

Conjugation of rFVIII with PSA Using the MAL-FMS-OSU Linker

For the preparation of rFVIII-PSA conjugate 6 ml of a solution of recombinant FVIII (4.5 mg/ml), derived from the Advate manufacturing process, in 20 mM Hepes buffer, pH 7.4 the bifunctional linker MAL-FMS-OSU (prepared as outlined by Tsubery et al., J Biol. Chem. 279, 38118-38124 (2004)) was added (concentration: 0.315 mg/mg protein) and incubated at R.T. for 30 min. Derivatized PSA containing a terminal SH group was prepared according to Example 1. The PSA derivative was added to the mixture (concentration: 27.8 mg PSA-SH/mg protein—450 fold molar excess) and incubated for additional 2 hours at R.T. The reaction was stopped by adding an aqueous solution of 0.1 M glycine (final concentration 10 mM) and 5 mM cysteine (end concentration 0.5 mM). The free reagents were separated from the rFVIII-PSA conjugate by Hydrophobic Interaction Chromatography using a prepacked Butyl Sepharose column (HiTrap Butyl FF 5 ml, GE Healthcare). A buffer containing 5 M NaCl (50 mM Hepes-buffer, 5M NaCl, 0.01% Tween 80, 6.7 mM $CaCl_2$, pH 6.9) was added to the PSA-rFVIII containing solution to give a final concentration of 3M NaCl. This mixture is applied to the column, which was subsequently washed with 10 CV equilibration buffer (50 mM Hepes-buffer, 3M NaCl, 0.1% Tween 80, 5 mM $CaCl_2$, pH 6.9) and the elution of the rFVIII-PSA conjugate was carried out with Citrate buffer, pH 7.4 (13.6 mM $Na_3$Citrate, 20 mM $CaCl_2$, 20 mM Histidine, 0.01% Tween 80). After elution of the conjugate the pH was adjusted to pH 6.9. The eluate contained 2.5 mg/ml protein (BCA assay).

The invention claimed is:
1. A process for the preparation of a compound of formula (2)

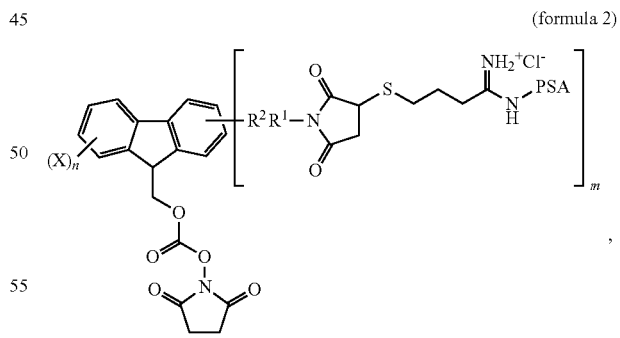

said process comprising the step of subjecting a compound of formula:

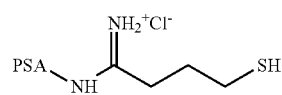

and an intermediate compound having a formula

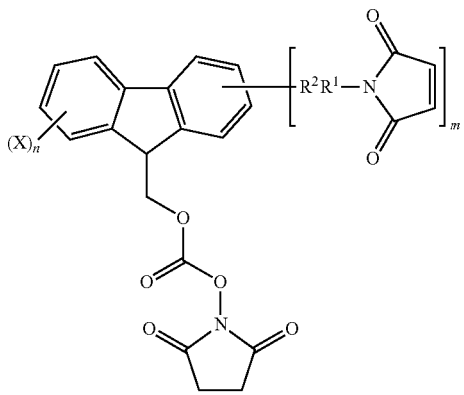

to a coupling reaction to form the compound of formula (2), wherein

PSA is polysialic acid;
$R^1$ is at each occurrence independently a $(C_1\text{-}C_8)$-alkyl;
$R^2$ is independently selected from the group consisting of —C(O)NR—, —C(O)NR—$(C_1\text{-}C_8)$-alkyl-NR—, —NRC(O)— and —NRC(O)—$(C_1\text{-}C_8)$-alkyl-NR,
R is independently either hydrogen or $(C_1\text{-}C_8)$-alkyl;
X is —$SO_3$—$R^3$;
$R^3$ is independently selected from the group consisting of hydrogen, $(C_1\text{-}C_8)$-alkyl and $(C_1\text{-}C_8)$-alkyl-$R^4$;
$R^4$ is a polymer,
n is an integer selected from 0, 1, 2, 3, or 4; and
m is an integer selected from 1, 2, 3, or 4.

2. The process according to claim 1, wherein $R^2$ is either —C(O)NR— or —NRC(O)— and wherein R is independently either hydrogen or $C_1\text{-}C_8$-alkyl.

3. The process according to claim 1, further comprising reacting the compound of formula (2) and a protein or peptide drug to form a protein or peptide drug conjugate having the formula:

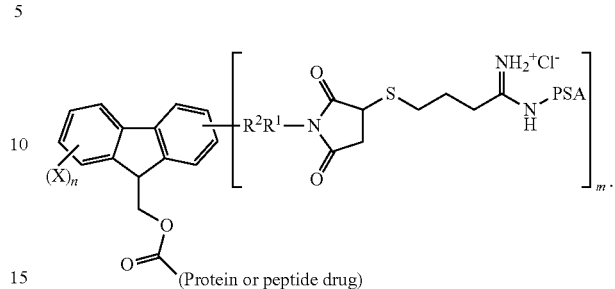

4. The process according to claim 3, wherein the protein or peptide drug is selected from the group consisting of Factor VII, von Willebrand Factor (VWF), Factor VIIa, Factor VIII, and Factor IX.

5. The process according to claim 1, wherein the PSA has a molecular weight of 5000 to 25000 Dalton.

6. The process according to claim 1, wherein the PSA has a molecular weight of 5000 to 10000 Dalton.

7. The process according to claim 3, wherein the PSA has a molecular weight of 5000 to 25000 Dalton.

8. The process according to claim 3, wherein the PSA has a molecular weight of 5000 to 10000 Dalton.

9. The process according to claim 5, wherein the PSA has a molecular weight of 5000 to 25000 Dalton.

10. The process according to claim 5, wherein the PSA has a molecular weight of 5000 to 10000 Dalton.

* * * * *

UNITED STATES PATENT AND TRADEMARK OFFICE
CERTIFICATE OF CORRECTION

PATENT NO.        : 8,445,544 B2                                    Page 1 of 1
APPLICATION NO.   : 12/688461
DATED             : May 21, 2013
INVENTOR(S)       : Turecek et al.

It is certified that error appears in the above-identified patent and that said Letters Patent is hereby corrected as shown below:

In the Claims

In Column 16, Line 31, in Claim 9, delete "claim 5," and insert -- claim 4, --, therefor.

In Column 16, Line 33, in Claim 10, delete "claim 5," and insert -- claim 4, --, therefor.

Signed and Sealed this
Twenty-third Day of June, 2015

Michelle K. Lee
*Director of the United States Patent and Trademark Office*